(12) United States Patent
Helzel et al.

(10) Patent No.: US 7,136,690 B2
(45) Date of Patent: Nov. 14, 2006

(54) ELECTRODE FOR BIOMEDICAL MEASUREMENTS

(75) Inventors: Thomas Helzel, Kaltenkirchen (DE); Fernando Suarez Sipmann, Madrid (ES); Gerd Kowalewski, Kaltenkirchen (DE)

(73) Assignees: Stephan Bohm, Hamburg-Eppendorf (DE); Marcelo B. P. Amato, Sao Paulo (BR)

( * ) Notice: Subject to any disclaimer, the term of this patent is extended or adjusted under 35 U.S.C. 154(b) by 47 days.

(21) Appl. No.: 10/848,501

(22) Filed: May 19, 2004

(65) Prior Publication Data

US 2005/0020935 A1 Jan. 27, 2005

Related U.S. Application Data

(63) Continuation of application No. PCT/EP02/13026, filed on Nov. 20, 2002.

(30) Foreign Application Priority Data

Nov. 20, 2001 (DE) .................................. 101 56 833

(51) Int. Cl.
*A61B 5/04* (2006.01)
(52) U.S. Cl. ..................... 600/372; 600/390; 600/547
(58) Field of Classification Search ................ 600/372, 600/506, 547
See application file for complete search history.

(56) References Cited

U.S. PATENT DOCUMENTS

| | | | | |
|---|---|---|---|---|
| 3,500,823 A | * | 3/1970 | Richardson et al. | 600/372 |
| 3,620,208 A | * | 11/1971 | Higley et al. | 600/395 |
| 3,882,846 A | | 5/1975 | Fletcher et al. | |
| 4,182,314 A | | 1/1980 | Boughton | |
| 4,617,939 A | * | 10/1986 | Brown et al. | 600/547 |
| 5,544,662 A | | 8/1996 | Saulnier et al. | |
| 5,709,213 A | | 1/1998 | Kruse et al. | |
| 6,016,445 A | | 1/2000 | Baura | |
| 6,236,886 B1 | | 5/2001 | Cherepenin et al. | |
| 6,718,191 B1 | * | 4/2004 | Eloranta et al. | 600/372 |

FOREIGN PATENT DOCUMENTS

| | | | |
|---|---|---|---|
| CA | 2280996 | * | 2/2001 |
| WO | WO 00/33733 | | 6/2000 |

OTHER PUBLICATIONS

Joseph D. Bronzino, The Biomedical Engineering Handbook, "Biopotential Electrodes", CRC Press 1995, pp. 745-757.

* cited by examiner

*Primary Examiner*—Lee S. Cohen
(74) *Attorney, Agent, or Firm*—Shlesinger, Arkwright & Garvey LLP (57) ABSTRACT

The invention relates to an electrode for biomedical measurements, in particular for measurements for electrical impedance tomography, which permits measurements with as little interference as possible. The electrodes comprise a contact plate, a line driver with a high-impedance signal input and low-impedance line output and a current source, with a current output and a reference point, whereby the contact plate is connected to the high-impedance signal input of the line driver and to the current output of the current source and the line driver and the current source are arranged in the vicinity of the contact plate.

14 Claims, 12 Drawing Sheets

ELECTRODE FOR BIOMEDICAL MEASUREMENTS

RELATED APPLICATIONS

This is a continuation of PCT/EP02/13026, filed Nov. 20, 2002, hereby incorporated by reference, which claims the priority benefit of German Application No. 101 56 833.9, filed Nov. 20, 2001, hereby incorporated by reference.

FIELD OF THE INVENTION

The invention relates to an electrode for biomedical measurements, in particular for measurements for electrical impedance tomography.

BACKGROUND OF THE INVENTION

In electrical impedance tomography for regional measurement of pressure-volume ratios, a number of electrodes are placed around the thorax, an alternating current, for example, in the range of 1 kHz to 1 MHz at an amplitude in the range of 1 µA to 10 mA being applied to respective adjacent electrodes. The other respective electrodes are used with the alternating current applied in order to carry out an impedance measurement relative to a defined reference potential. As soon as all the electrodes have been used in turn as current-conducting electrodes, a cycle is completed for data acquisition. In order to eliminate statistical interferences, a plurality of data acquisition cycles are generally averaged in order to obtain a corresponding image. The largest impedance changes in the region of the thorax are produced by the inhalation and exhalation of air. It can be observed in the process that the impedance change measured by the electrodes is a measure for the volume change in the lung. A two-dimensional or even three-dimensional image of the impedance changes can be constructed on the basis of a computer-assisted evaluation of the signals at the electrodes.

The artificial respiration of the diseased lung in which oedemas have formed is a particular problem as it cannot be precisely monitored whether the lung is already closed or collapsed in certain parts. It has been found in this instance that the mortality rate can be substantially lowered if a specific pressure, which just allows all the alveoli to be kept open is artificially maintained in the lung.

For this purpose, WO 00/33733 describes how the alveolar opening and the alveolar closing of the lung can be determined as a function of the respiratory pressure from the measured impedance changes by electrical impedance tomography. However, in this vital application, relatively large measuring errors have to be ruled out as far as possible.

Important measuring errors in electrical impedance tomography are based on the changing impedances of the feed lines to the electrodes and the transition resistances between the skin of the patient and the electrodes. As these interfering impedances are located in series to the impedance to be measured, the interfering impedances directly enter the measurement as errors.

U.S. Pat. No. 5,544,662 describes various measures in terms of circuitry for an evaluation apparatus to reduce the above-mentioned measuring errors. The respective electrodes, however, continue to be connected via feed lines which lead from the electrodes to an evaluation apparatus set up next to the patient, so measuring errors continue to occur owing to impedance changes at the feed lines.

J. D. Bronzino, The Biomedical Engineering Handbook, CRC Press, 1995, pages 745 to 757 describes various types of so-called biopotential-electrodes which are designed as passive electrodes to pick up potentials on the body. It is also mentioned inter alia, that operation amplifiers configured as isolation amplifiers can be integrated on the electrode. Further wiring of the electronics integrated in the electrode is not mentioned, however. This is primarily because the electrodes have to be used as disposable articles for reasons of hygiene and therefore an expensive wiring of the electrode is out of the question for reasons of cost.

OBJECTS AND SUMMARY OF THE INVENTION

The object of the invention is to provide an electrode for biomedical measurements and in particular for measurements with electrical impedance tomography which allows measurements which are as free of interference as possible with economical production.

The electrode according to the invention comprises a contact plate, a line driver which has a high-impedance signal input and a low-impedance line output, and a current source which has a current output and a reference point, wherein the contact plate is electrically connected to the high-impedance signal input of the line driver and to the current output of the current source and wherein the line driver and current source are arranged in the vicinity of the contact plate.

The essential recognition of the invention consists in that the combination of a line driver and a current source as integrated electronics on or in the vicinity of the contact plate already allows a substantial increase in accuracy compared to known electrodes with continuing low production costs. The production of an integrated electrode as a disposable part is therefore possible with feasible costs.

The electrode according to the invention is suitable for all biomedical measurements in which a current is applied via the contact plate and a potential is measured via the contact plate, as is the case, for example, in electrical impedance tomography. The invention is based in this instance on the recognition that both the current supply to the contact plate and the measured value acquisition from the contact plate has to take place in the vicinity of the contact plate. This is achieved by a high internal resistance of the current source and a high input resistance of the line driver, so the interferences on the lines can be disregarded for the external current supply and for relaying the measured signals. The proximity of the current source and the line driver to the contact plate is defined by the dimension of the contact plate. Proximity in the sense of the invention no longer exists at least when 10 times the spatial dimension of the contact plate is exceeded.

According to a preferred embodiment, it is preferred that the electrical connections between the contact plate, the current source as well as the line driver are designed in such a way that a stray capacitance which is as low as possible is produced between the contact plate and reference point. It is particularly advantageous here if the line driver and the current source are located on the contact plate as integrated circuit, as the feed line length between the contact plate and the line driver and current source can be kept to a minimum. A further measure may consist in that the contact plate with the line driver and the current source are integrated in a screened housing.

According to a further preferred embodiment, a circuit is provided for active compensation of the stray capacitance between the contact plate and reference point. In this manner, line length between the contact plate and the current source and the line driver can be permitted within certain limits, it being possible to eliminate stray capacitances being produced by means of the compensation circuit.

According to a further preferred embodiment, it is provided that the current source is a bipolar current source with high internal resistance, the output current of which is virtually proportional to the input voltage. Bipolar current sources have the advantage of a particularly high internal resistance and are therefore particularly suitable for the present application.

According to a further preferred embodiment, it is provided that the current source supplies an alternating current with frequencies in the range of 1 kHz to 1 MHz and amplitudes in the range of 1 µA to 10 mA. Currents with these characteristics are used predominantly in electrical impedance tomography. However, the invention is obviously not limited to these characteristics. It is also conceivable to use various current sources with various characteristics which supplement or overlap each other in their signal ranges. It is also conceivable that the alternating current should be frequency-modulated and/or amplitude-modulated.

According to a further preferred embodiment it is provided that the line driver consists of an impedance converter circuit. Impedance converter circuits are variously known and transform a high input resistance into a low line resistance.

According to a further preferred embodiment it is provided that a voltage measuring apparatus is connected between the low-impedance line output and the reference point. Measurements by electrical impedance tomography can be carried out in this manner, for example, in that a current is applied via the electrode and the resulting voltage is picked up at the electrode. It is particularly advantageous in this context if, between the contact plate and the reference point, a switch is provided, via which the contact plate can be optionally switched to the potential of the reference point. A specific electrode or a plurality of electrodes can thus be excluded from the measurement. Calibration of the voltage measurement compared to the reference point can be undertaken simultaneously.

The electrode belt according to the invention for carrying out a measurement by electrical impedance tomography consists of a large number of electrodes according to the invention. The electrodes are, in this instance, preferably provided at virtually the same spacing from one another. The measured values can be particularly reliably detected and transmitted by a digital data acquisition unit. For this purpose, at least one analogue-to-digital converter is provided which from one or a plurality of electrodes reads in the voltage between the respective contact plate and the reference point and passes it to a central processor via a data line.

Obviously, the embodiments described above and/or listed in the sub-claims are not only usable in the respectively disclosed combination but also in other combinations or alone.

BRIEF DESCRIPTION OF THE DRAWINGS

The invention will be described hereinafter in more detail with the aid of various embodiments with reference to the accompanying drawings, in which.

DETAILED DESCRIPTION OF THE INVENTION

Figure 1:
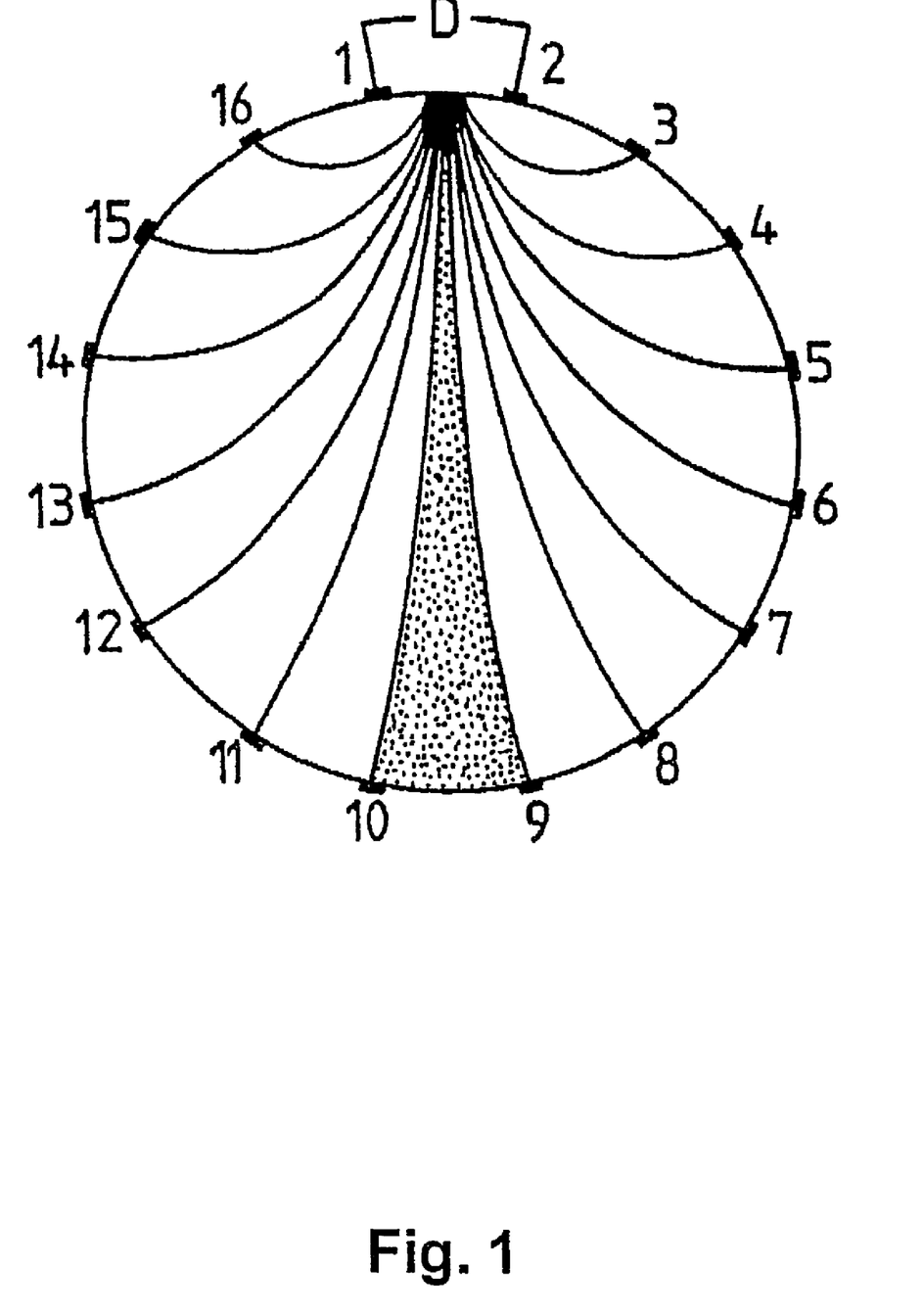
FIG. 1 shows a section through a thorax with an electrode configuration according to the prior art.

FIG. 1 shows a section through a thorax with an electrode configuration according to the prior art (U.S. Pat. No. 5,626,146). 16 electrodes are arranged around the thorax with virtually equal spacing. A current is applied between the electrodes 1 and 2. The curved lines are then lines of the same potential with reference to the electrodes 1 and 2 acting as a dipole. The voltage potentials measured at the electrodes 3 to 16 can be traced back along these lines in order to establish the resistance value at points on these lines. Once the respective measurements have been carried out for all possible dipoles, the impedance values determined from each measurement can be accordingly superimposed. This tracing method was selected as an example here and is obviously only one alongside many possible methods of image reconstruction according to the principle of electrical impedance tomography.

Figure 2:
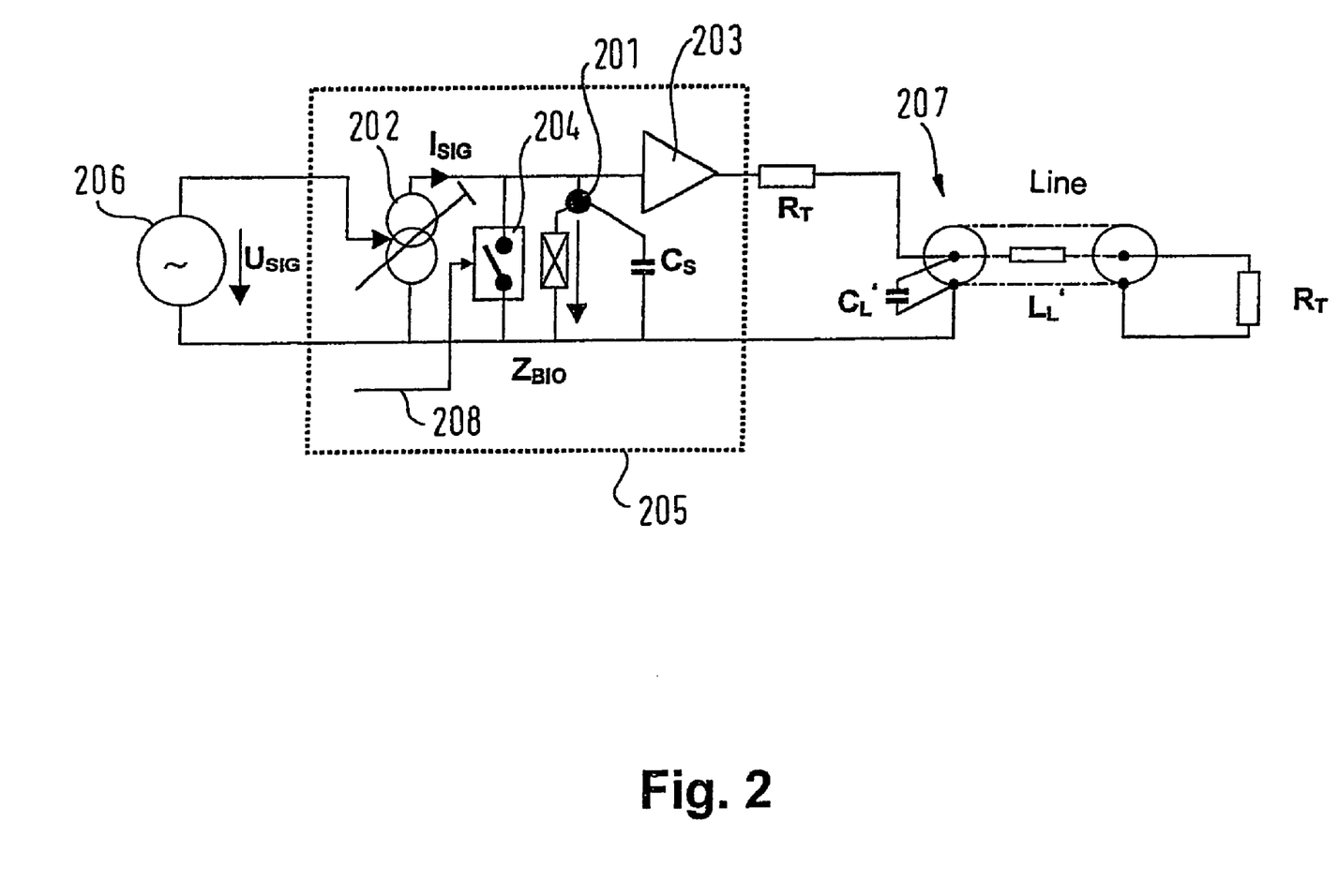
FIG. 2 shows a schematic diagram of an electrode according to the invention.

FIG. 2 shows a schematic diagram of an electrode according to the invention. According to its basic structure, the electrode consists of a contact plate 201, a current source 202 and a line driver 203. The contact plate 201 is connected, on the one hand, to the current output of the current source 202 and, on the other hand, to the high-impedance input of the line driver 203. The current source 202 is connected by its other pole to a reference potential, the current $I_{SIG}$ of the current source being virtually proportional to the input voltage $U_{SIG}$ supplied by a voltage source 206. The contact plate 201 rests on the skin of the patient, the impedance $Z_{BIO}$ being measured between the electrode and reference potential. It is the aim of the entire circuit to keep the interfering load impedances caused by stray capacitances $C_s$ and resistive shunts between the contact plate 201 and reference potential as small as possible. Also provided between the contact plate and reference potential is a controllable switch 204 which can be controlled via the control line 208 and with which the contact plate 201 can be connected to the reference potential. Individual electrodes can thus be excluded from the measurement or else a calibration of the impedance measurement can be carried out. The voltage between the electrode and reference potential is measured at the output of the line driver 203. The measurement is optionally carried out via a line 207 which is shown in FIG. 2 with its corresponding replacement circuit diagram. The dashed part 205 of the circuit is generally accommodated on the contact plate 201, while the voltage source 206 or the line 207 may lie further away from the contact plate 201 without causing noteworthy interferences or measuring errors.

Figure 3A:
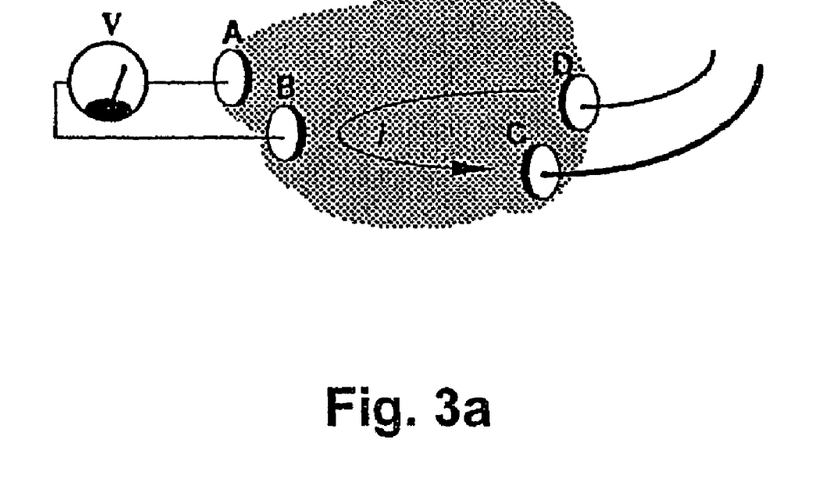
FIG. 3 shows a schematic view of the reciprocal technique.
Figure 3B:
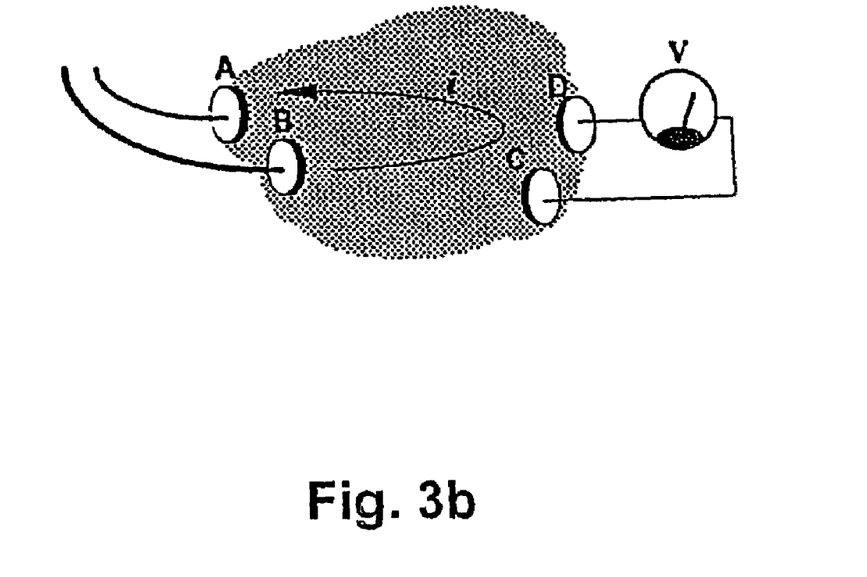

FIG. 3 shows a schematic view of the reciprocal technique. In FIG. 3a, a current is applied via the electrodes C and D and the resulting voltage is measured at the electrodes A and B. Conversely, in FIG. 3b a corresponding current is applied via the electrodes A and B and the resulting voltage measured at the electrodes C and D. It can be shown that the respectively measured voltages from FIG. 3a and FIG. 3b must be the same. This so-called reciprocal technique can, for example, be used to check the contacts on the electrodes to the skin of the patient, in a simple manner. The respectively desired electrodes can in the process be selected from the electrodes shown in FIG. 1 by controlling the switch 204 according to FIG. 2.

Figure 4:
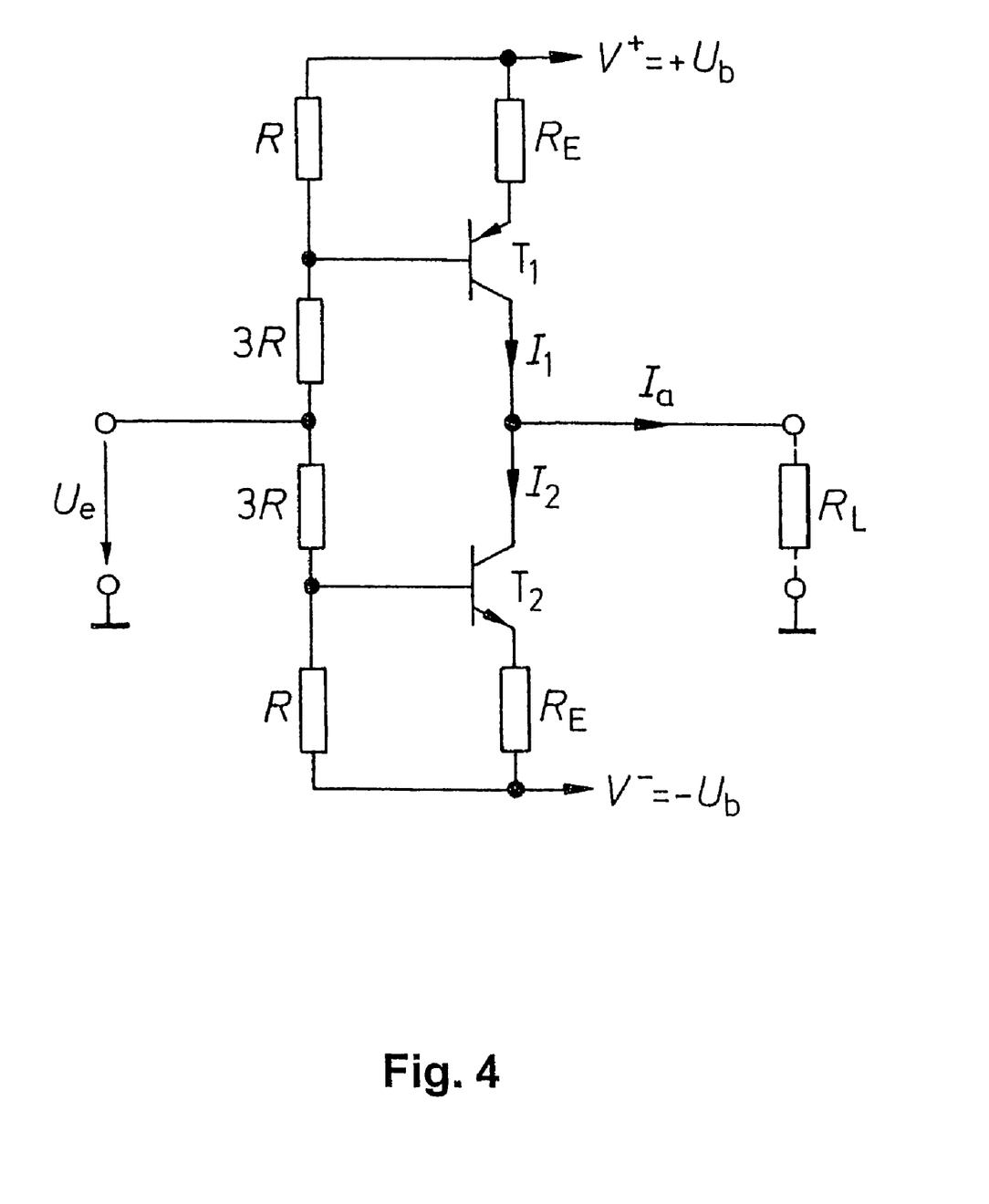
FIG. 4 shows a circuit diagram for a bipolar current source.

FIG. 4 shows a circuit diagram for a bipolar current source which, for example, may be used as the current source 202 according to FIG. 2. When $U_e=0$, the two currents $I_1$ and $I_2$ are the same size and the output current is zero. If a positive input voltage is applied, $I_2$ increases and $I_1$ reduces with the result that a negative output current flows. In the case of negative input voltages the circuit behaves in the reverse manner.

Figure 5:
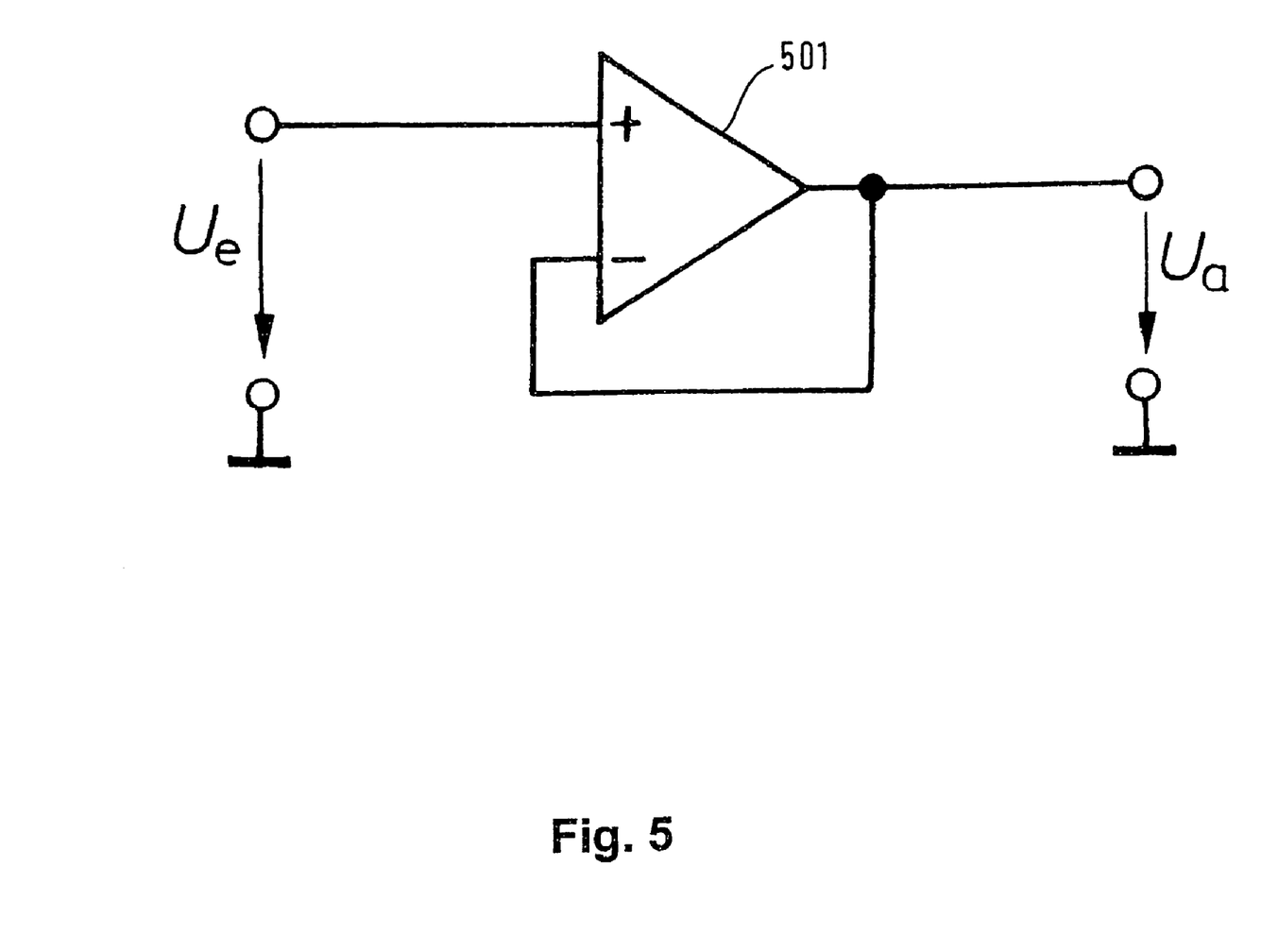
FIG. 5 shows a circuit diagram for a line driver.

FIG. 5 shows a circuit diagram for a line driver which, for example, may be used as a line driver 203 according to FIG. 2. The operation amplifier 501 is accordingly wired as an isolation amplifier, so a voltage ratio 1 is produced between the output and input voltage. An isolation amplifier of this type has a high input resistance with a low output resistance, the offset between input and output voltage only being a few mV.

Figure 6:
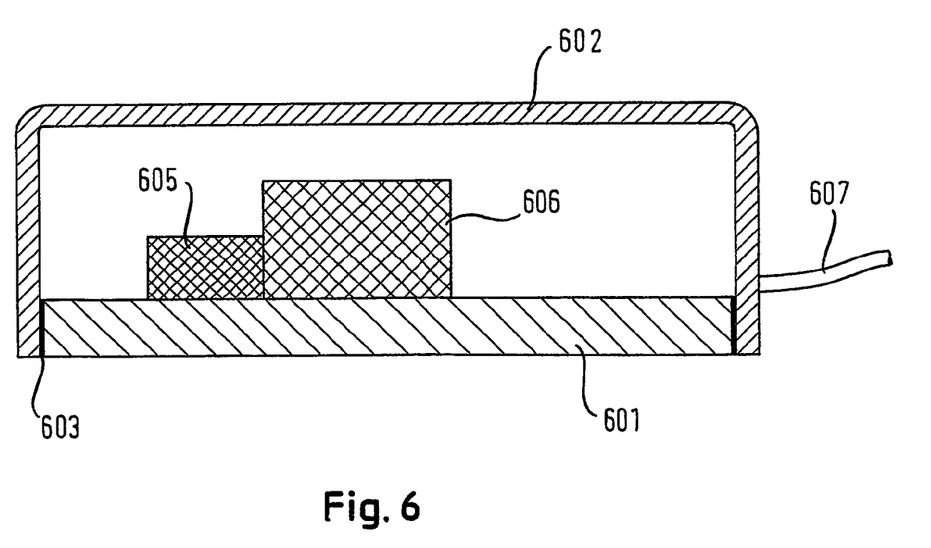
FIG. 6 shows a section through an electrode according to the invention according to the schematic diagram according to FIG. 2.

FIG. 6 shows a section through an electrode according to the invention according to the schematic diagram of FIG. 2. Viewed electrically, the part shown here corresponds to the circuit part 205 shown by dashed lines according to FIG. 2. The contact plate 601 is surrounded by the housing 602 which may have a screening effect and can be arranged for reference potential. In this case, an insulation 603 is introduced between the contact plate 601 and the housing 602. An integrated circuit which is shown by the units 605, 606 and in which the circuit part 205 according to FIG. 2 is implemented is located on the contact plate. The entire circuit part is optionally already accommodated in an integrated electric circuit. It is also conceivable for the contact plate 601 to also be accommodated in this integrated electric circuit underneath. The electrical feed and discharge lines are guided in the cable 607.

Figure 7:
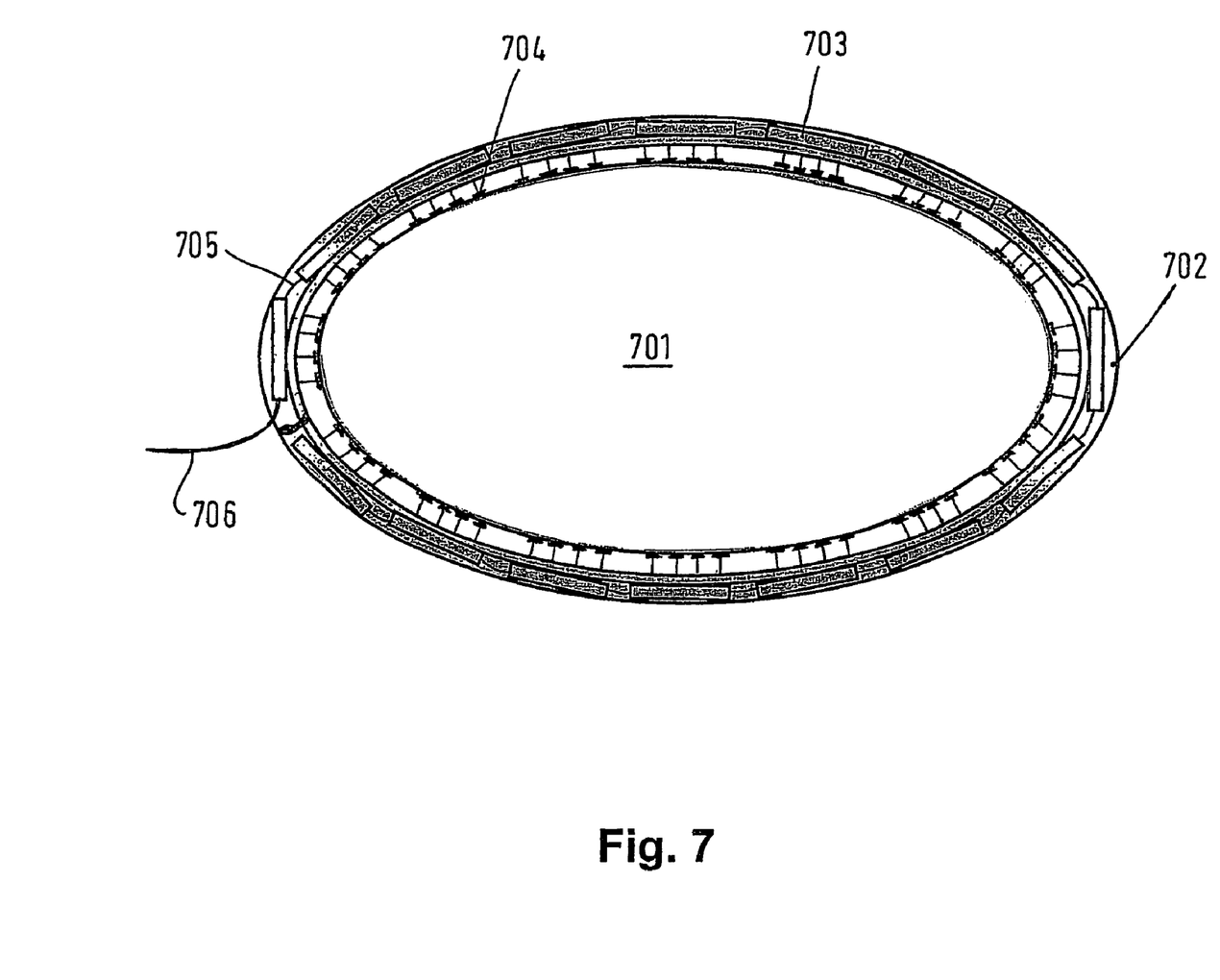
FIG. 7 shows a section through an electrode belt according to the invention.

FIG. 7 shows a section through an electrode belt according to the invention. The electrode belt 702 is placed around the thorax 701 of the patient. A large number of electrodes 704 are provided on the inside, four electrodes, in each case, being connected to a data acquisition unit 703. The data acquisition units 703 are connected to one another by connection lines 705, the electrical feed and discharge lines being guided in the cable 706.

Figure 8:
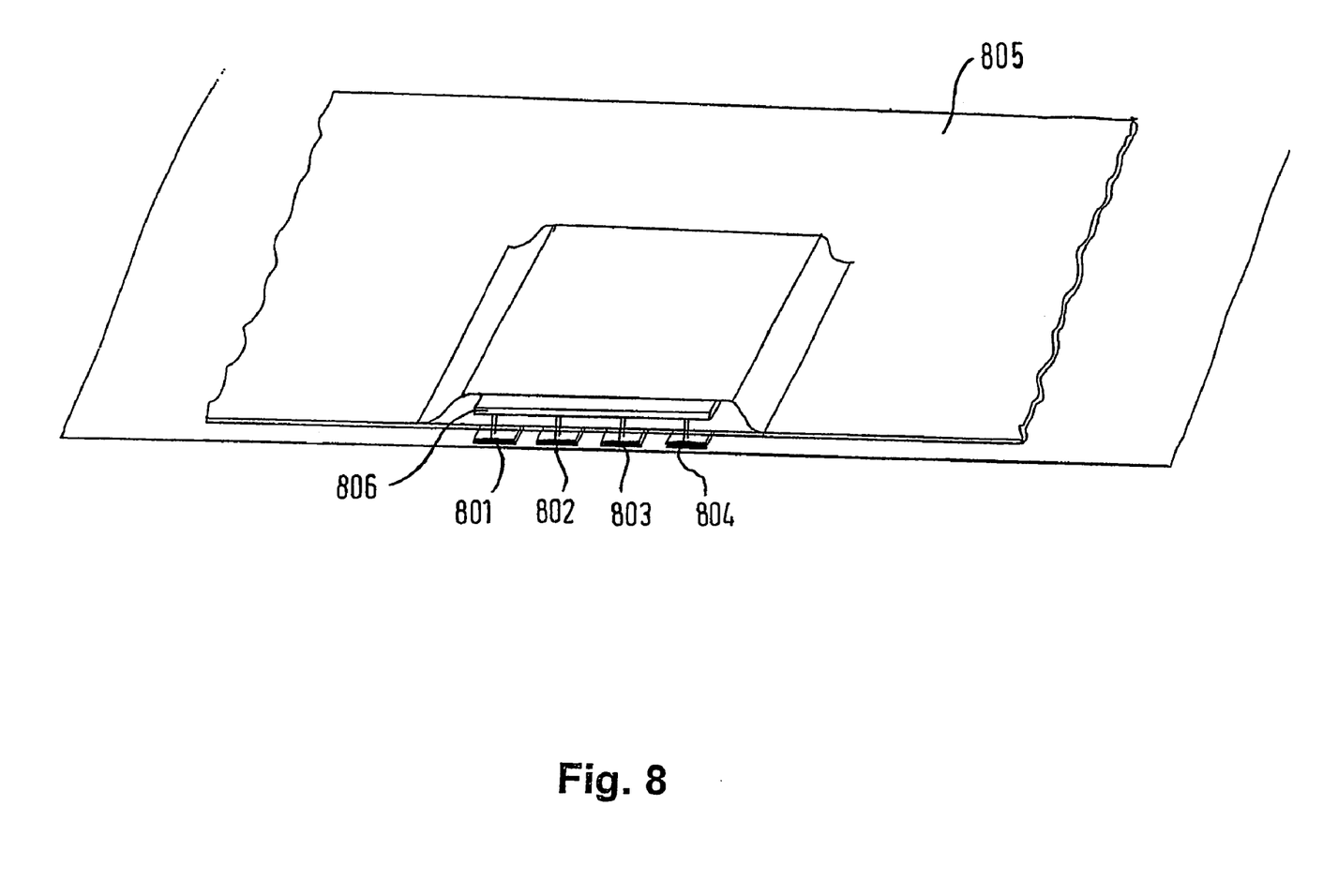
FIG. 8 shows a section through a data acquisition unit of the electrode belt according to FIG. 7.

FIG. 8 shows a section through a data acquisition unit of the electrode belt according to FIG. 7. Four electrodes 801, 802, 803 and 804 are fastened to the lower edge of the belt material 805 and electrically connected to the evaluation electronics 806. In the case of the evaluation electronics, various forms of data acquisition are possible:

Parallel method: each channel is digitised synchronously by means of its own analogue-to-digital converter (ADC). The respective conversion result is optionally available in parallel in a respective local digital memory for transfer via a digital data bus structure for further signal processing.

Analogue-multiplex: in the time-division multiplex method, all measuring channels are connected individually per multiplexer according to an established scheme to a single powerful ADC and digitised by it. An external digital memory, after transfer via a data interface, receives all consecutive data in a value table.

Integrated data acquisition: a monolithically integrated data acquisition system, consisting of an input channel multiplexer integrated on a microchip, an amplifier with optional amplification factor, a downstream analogue-to-digital converter, a local memory for receiving a larger number of digitalised measured values, and an autonomous sequence control, connected to a communications interface or the data bus of a host computer, independently and sequentially detects a number of input channels and stores the digitised measured values in the local memory. On reaching a certain degree of filling of the memory, the host computer is induced to quickly adopt the acquired data. There is therefore space again for further data of the digital-to-analogue converter in the local memory. The computer system set up next to the patient is thus effectively relieved by a partially autonomously operating data acquisition system of this type.

Figure 9:
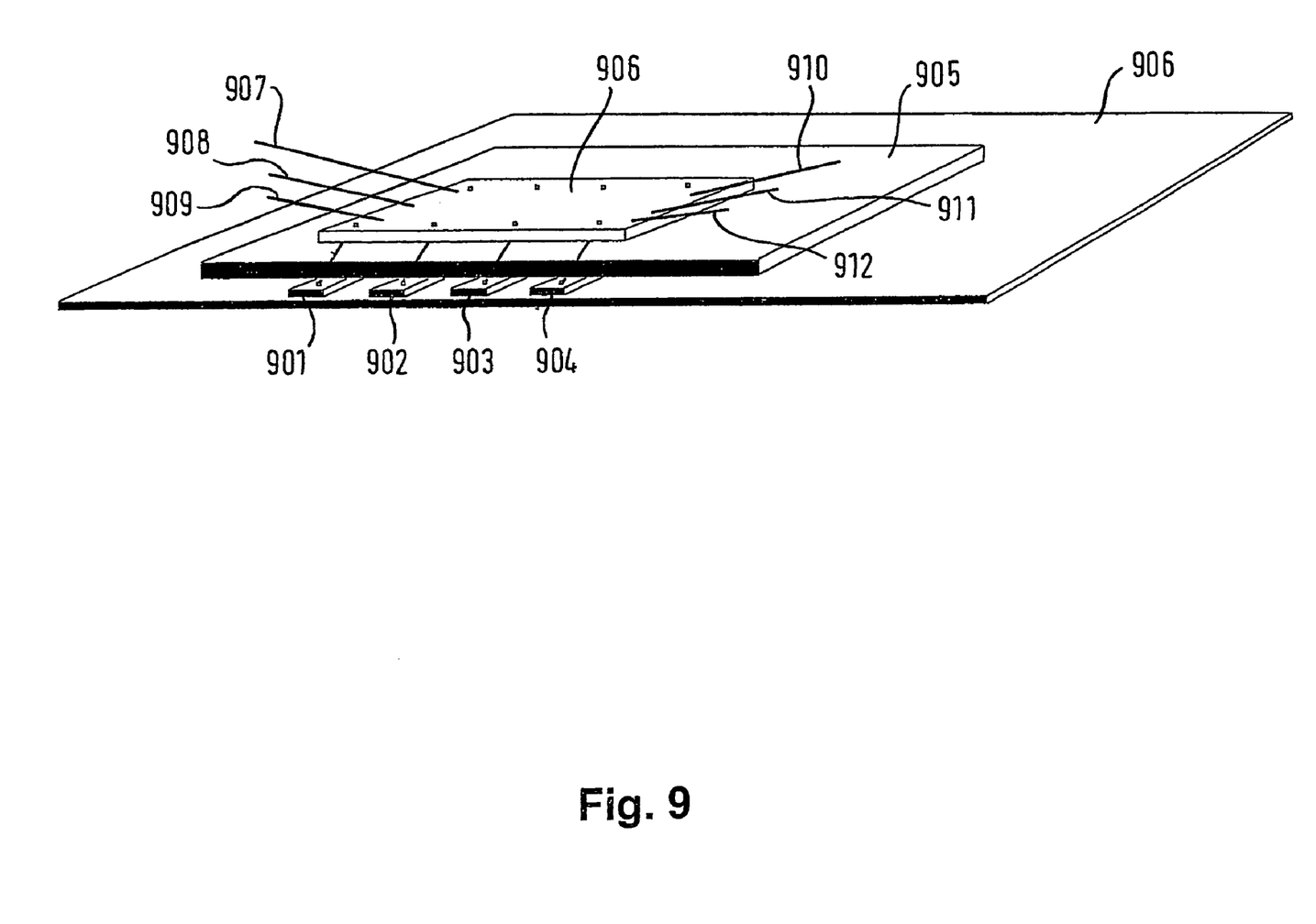
FIG. 9 shows an exploded view of the data acquisition unit shown in FIG. 8.

FIG. 9 shows an exploded view of the data acquisition unit shown in FIG. 8. The contact plates 901, 902, 903 and 904 are fastened to the belt material 905 and lie on the skin 906 of the patient. The data acquisition unit 906 with corresponding through-platings to the contact plates 901, 902, 903 and 904 is located on the other side of the belt material. The lines 907 to 912 are contact lines to the respective adjacent data acquisition units (signal input 907, supply voltage input 908, control lines 909, data output 910, supply voltage output 911 and control line 912).

A key variable for use in electrical impedance tomography is a signal-to-noise ratio which is as large as possible. For this purpose, a, as far as possible, low-impedance, symmetrical signal transmission is proposed. As a consequence this means extension by corresponding symmetrical buffers at the electrode output and symmetrical line receivers together with terminating resistors on the transmitting side.

Figure 11:
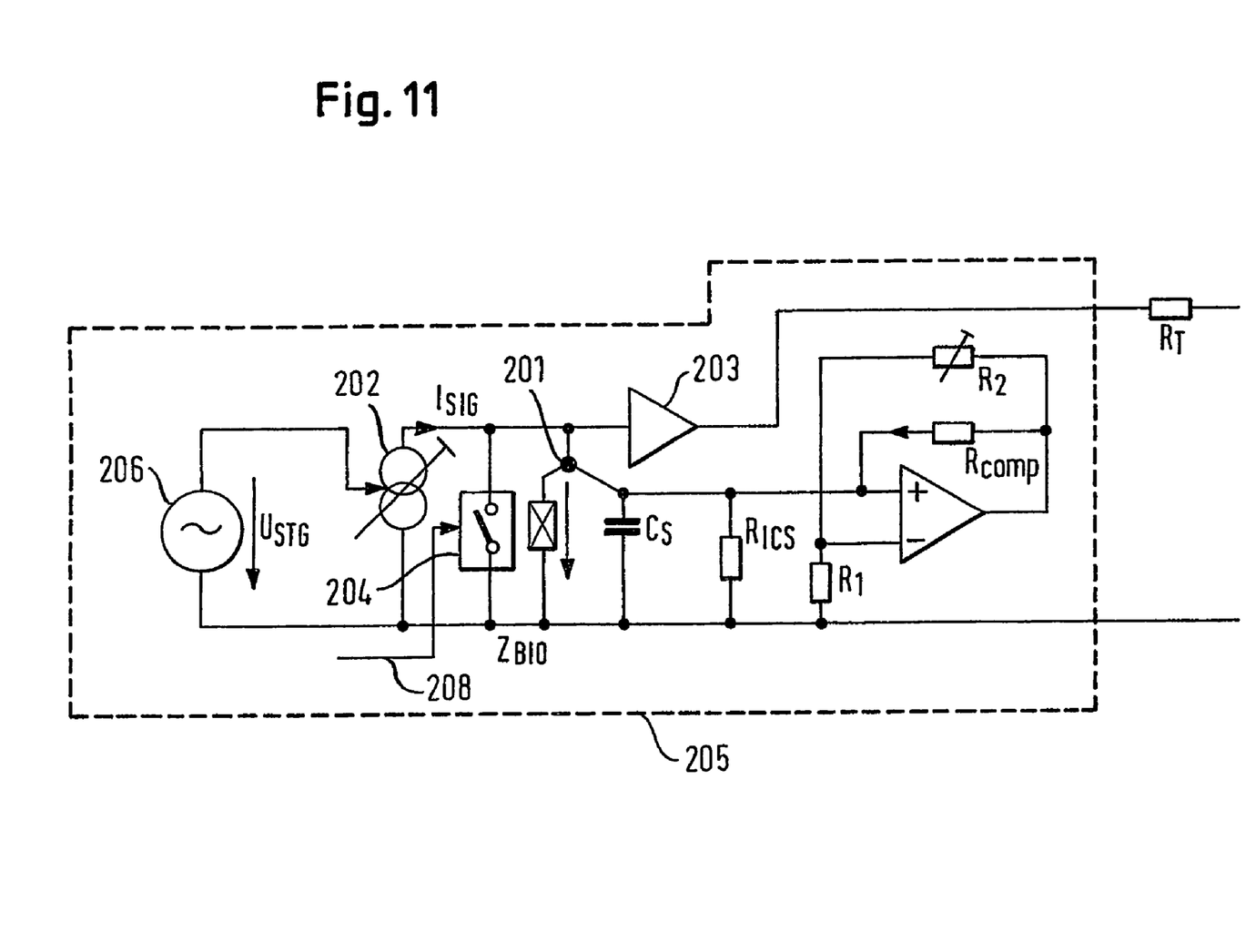
FIG. 11 shows a circuit for compensating the high-impedance internal resistance of the alternating current source impedance of an alternating current source and FIG. 12 shows a circuit for compensation of stray capacitances at the electrode connection point of the electrode.
Figure 12:
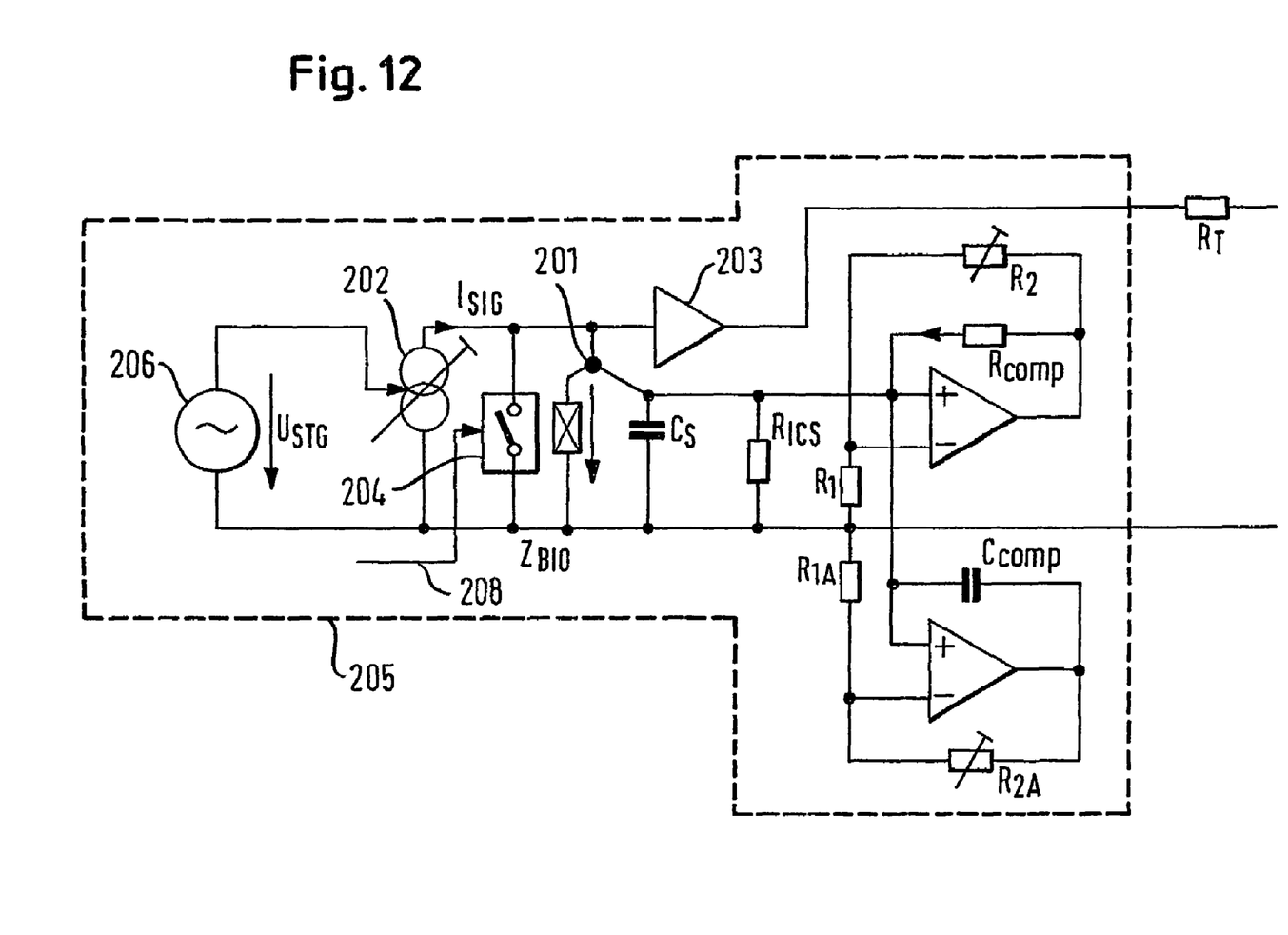

A compensation or partial compensation of the parasitic capacitances and the remaining effective internal resistances of the current sources is proposed in the embodiments according to FIG. 11 and FIG. 12. This compensation or partial compensation may be active and/or resistive and/or capacitive.

1. Low-impedance, symmetrical signal transmission and processing:

The signal-to-interference ratio to the electrodes can be improved by, a) a symmetrical signal transmission with b) low-impedance terminating impedances ($R_{Ti}$ with $T_{Ti}<=300$ typ. Ohm) and c) improved decoupling of the current supply and multiplexer structures.

Figure 10:
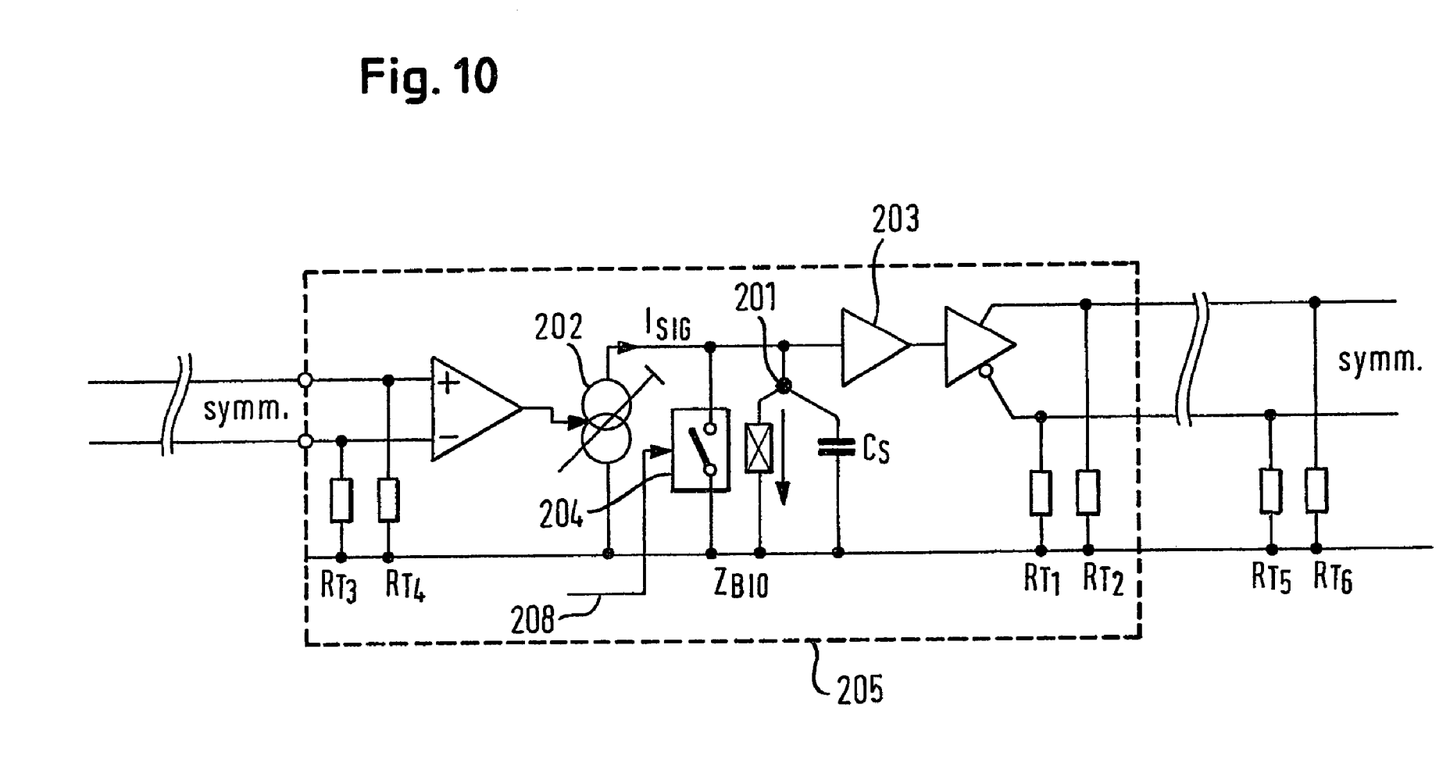
FIG. 10 shows a circuit for low-impedance, symmetrical signal transmission and processing.

FIG. 10 shows a corresponding circuit:

A line receiver (differential amplifier) suitable for symmetrical signal transmission technology is added upstream from the control input of the alternating current source 202. The symmetrical line termination is achieved with the low-impedance terminating impedances ($R_{T3}$, $R_{T4}$).

A symmetrical line driver is correspondingly added at the output of the buffer 203. With the associated low-impedance terminating resistances ($R_{T1}$, $R_{T2}$) and ($R_{T5}$, $R_{T6}$) for the double termination at the beginning and end of a relatively long line, a low-impedance line system which is very favourable and advantageous overall is created so that interfering influences which are injected into the symmetrical line system are largely subtracted in the respective line receivers.

The time constants of the switching transients, formed for example by loaded input capacitances and the input or output impedances of the line system are further advantageously influenced very favourably. Moreover, the risk of capacitance interference couplings with noteworthy amplitudes on the very low resistance conductors is also substantially hindered.

Overall, a supplement is produced which has increased line outlay but at the same time is advantageous in many respects, which leads to substantially more favourable S/N values.

2. Compensation of the high-impedance internal resistance of the alternating current source impedance of an alternating current source.

The compensation method which can also be applied, outlined in FIG. 11, for an at least partially possible compensation of the high-impedance real source resistance ($R_{ICS}$) of an alternating current source as a proportion of the complex alternating current source impedance can be explained in terms of its function as follows:

The additional operation amplifier with its wiring elements R1, R2 and $R_{COMP}$ are a compensation circuit here for the positive source resistance $R_{ICS}$.

The operation amplifier connected with its non-inverting input to the node 201 can, with a deliberate omission of $R_{COMP}$ initially be understood as a non-inverting basic circuit, the voltage amplification of which from this input to the output of the wiring is determined by the resistances R1 and R2 according to U_OUT/U_IN=1+R2/R1. The ratio of R2/R1 thus determines the level of the output voltage U_OUT at its output. If the ratio to R2/R1=1, the voltage amplification U_OUT/U_IN=+2 is produced.

If the voltages and currents around the source resistance $R_{ICS}$ are observed, a positive partial flow is produced by $R_{ICS}$, according to I=U/R. A further real current proportion could optionally also be produced by the bio-impedance $Z_{BIO}$ also connected in parallel according to the rules of current division. $Z_{BIO}$ would initially be assumed here as a pure reactance.

If the resistance $R_{COMP}$ connected from the output of the operation amplifier to nodes 201 is observed, a further current path is produced for each voltage differential between the node 201 and the output voltage of the operation amplifier which is determined by the resistance ration R2/R1.

The output voltage will therefore be precisely twice the amount of the voltage at nodes 201 for the assumption of a voltage amplification of the OPAMPs of U_OUT/U_IN=+2. If the resistance value of $R_{COMP}$ is selected so as to be identical to $R_{ICS}$, the real partial flows flowing via $R_{COMP}$ to the node 201 and flowing away via $R_{ICS}$ are compensated precisely on the basis of the same amounts but opposite signs: the OPAMP circuit around $R_{COMP}$ allows this to appear negative, so $R_{ICS}-R_{COMP}=0$ applies or, expressed as a reciprocal of the conductances for the resulting parallel circuit Rp $1/(1/R_{ICS}-1/R_{COMP})=Rp.$ For the identity $R_{ICS}=R_{COMP}$ a 0 is produced in the denominator of this fraction—a pole for the resistance value of the expression.

By the selection of $R_{COMP}$ or the resistance ratio R2/R1 for the selection of the voltage amplification, there can be an over-compensation or an under-compensation. The first case leads to instability and an unusable oscillation of the circuit.

Under-compensation, however, allows the very advantageous, gradually adjustable artificial increase in the source impedance of the current source, with the preference of a qualitatively substantially increased precision for corresponding voltage measurements via a buffer 203.

Moreover, the method also allows the compensation of further real resistances connected in parallel and is therefore universally usable.

3. Compensation of stray capacitances at the electrode connection point of the electrode FIG. 12 shows the method expanded for capacitative compensation. All capacitances connected in parallel can thus, in turn, be combined into one which can then be largely compensated substitutionally: $C_{COMP}=(C_{ICS}+C_S)$ The circuit according to FIG. 12 differs from the circuit according to FIG. 11 in that instead of a real source resistance $R_{ICS}$, a capacitance to be compensated ($C_{ICS}+C_S$) with its reactance $X_{ICS}=\frac{1}{2}*PI*f*(C_{ICS}+C_S)$ is now used, and instead of the resistive element $R_{COMP}$ a reactance $X_{COMP}=\frac{1}{2}*PI*f*C_{COMP}$ is now used.

In this instance, the variable f is in each case the operating frequency of the circuit.

With the double approach shown for resistive and capacitative partial compensation, the parasitic influences even of an active probe are to be substantially further reduced and the usable frequency range of the originally conceived operating frequency of 10 kHz or 25 kHz is to be extended even beyond 100 kHz.

We claim:

1. Electrode for biomedical measurements, with a contact plate, and with a line driver which has a high-impedance signal input and a low-impedance line output and is arranged in the vicinity of the contact plate, wherein a current source which has a current output and a reference point and is arranged in the vicinity of the contact plate, wherein the contact plate is electrically connected to the high-impedance signal input of the line driver and to the current output of the current source and wherein a measuring circuit voltage can be picked up between the low-impedance line output and the reference point.

2. Electrode according to claim 1, wherein the electrical connections between the contact plate, the current source and the line driver are designed in such a way that a stray capacitance which is as low as possible is produced between the contact plate and reference point.

3. Electrode according to claim 1, wherein the line driver and the current source are located as integrated circuit on the contact plate.

4. Electrode according to claim 1, wherein the contact plate with the line driver and the current source are integrated in a shielded housing.

5. Electrode according to claim 1, wherein a circuit is provided for active compensation of the stray capacitance between the contact plate and reference point.

6. Electrode according to claim 1, wherein the current source is a bipolar current source with high internal resistance, the output current of which is virtually proportional to the input voltage.

7. Electrode according to claim 1, wherein the current source supplies an alternating current with frequencies in the range from 1 kHz to 1 MHz and amplitudes in the range from 1 µA to 10 mA.

8. Electrode according to claim 7, wherein the alternating current is frequency-modulated and/or amplitude-modulated.

9. Electrode according to claim 1, wherein the line driver consists of an impedance converter circuit.

10. Electrode according to claim 9, wherein a voltage measuring apparatus is connected between the low-impedance line output and the reference point.

11. Electrode according to claim 1, wherein a switch, via which the contact plate can be optionally switched to the potential of the reference point, is provided between the contact plate and reference point.

12. Electrode belt for carrying out a measurement by electrical impedance tomography with a plurality of electrodes, each electrode comprises a contact plate and a line driver which has a high-impedance signal input and a low-impedance line output and is arranged in the vicinity of the contact plate, wherein a current source which has a current output and a reference point and is arranged in the vicinity of the contact plate, wherein the contact plate is electrically connected to the high-impedance signal input of the line driver and to the current output of the current source and wherein a measuring circuit voltage can be picked up between the low-impedance line output and the reference point.

13. Electrode belt according to claim 12, wherein the electrodes are provided with virtually equal spacing from one another.

14. Electrode belt according to claim 12, wherein data acquisition units with at least one analogue-to-digital converter are provided which from one or more electrodes read in the voltage between the respective contact plate and the reference point via the analogue-to-digital converter and pass it to a central processor via a data line.

* * * * *